United States Patent [19]
Lenarz et al.

[11] Patent Number: 6,141,591
[45] Date of Patent: Oct. 31, 2000

[54] MAGNETLESS IMPLANTABLE STIMULATOR AND EXTERNAL TRANSMITTER AND IMPLANT TOOLS FOR ALIGNING SAME

[75] Inventors: Thomas Lenarz; Benno P. Weber; Jurgen Neuburger, all of Hannover, Germany

[73] Assignee: Advanced Bionics Corporation, Sylmar, Calif.

[21] Appl. No.: 09/142,293

[22] PCT Filed: Mar. 4, 1997

[86] PCT No.: PCT/US97/03394

§ 371 Date: May 10, 1999

§ 102(e) Date: May 10, 1999

[87] PCT Pub. No.: WO97/32629

PCT Pub. Date: Sep. 12, 1997

Related U.S. Application Data

[60] Provisional application No. 60/012,910, Mar. 6, 1996.

[51] Int. Cl.[7] .......................... A61N 1/372; A61N 1/378
[52] U.S. Cl. .............................. 607/57; 607/55
[58] Field of Search ................. 607/55–57, 137

[56] References Cited

U.S. PATENT DOCUMENTS

| | | |
|---|---|---|
| Re. 31,031 | 9/1982 | Kissiah, Jr. . |
| Re. 32,947 | 6/1989 | Dormer et al. . |
| 4,019,518 | 4/1977 | Maurer et al. . |
| 4,207,441 | 6/1980 | Ricard et al. . |
| 4,267,410 | 5/1981 | Forster et al. . |
| 4,428,377 | 1/1984 | Zollner et al. . |
| 4,495,917 | 1/1985 | Byers . |
| 4,532,930 | 8/1985 | Crosby et al. . |
| 4,726,378 | 2/1988 | Kaplan . |
| 4,819,647 | 4/1989 | Byers et al. . |
| 4,991,582 | 2/1991 | Byers et al. . |
| 5,531,774 | 7/1996 | Schulman et al. . |
| 5,545,191 | 8/1996 | Mann et al. ........................... 607/57 |
| 5,549,658 | 8/1996 | Shannon et al. ...................... 607/57 |
| 5,571,148 | 11/1996 | Loeb et al. . |
| 5,690,693 | 11/1997 | Wang et al. ........................... 607/61 |
| 5,749,909 | 5/1998 | Schroeppel et al. .................. 607/33 |
| 5,948,006 | 9/1999 | Mann .................................... 607/61 |

*Primary Examiner*—Carl H. Layno
*Attorney, Agent, or Firm*—Bryant R. Gold

[57] ABSTRACT

An implantable receiver (12) is powered and controlled by an external (not-implanted) transmitter (14) when a transmitter coil (22) is properly aligned with a receiver coil (20). No magnets are used in either the transmitter or receiver to achieve and maintain the needed alignment. Rather, a special set of implant tools (50) are used to assure that alignment is achieved and maintained between the implantable receiver (12) and external transmitter (14) when the implant operation is carried out. A preferred embodiment of the invention provides a magnetless implantable cochlear stimulator (ICS) (40) and a corresponding magnetless headpiece (30) worn behind the ear.

9 Claims, 7 Drawing Sheets

MAGNETLESS IMPLANTABLE STIMULATOR AND EXTERNAL TRANSMITTER AND IMPLANT TOOLS FOR ALIGNING SAME

This application is a International 371 of PCT/US97/03394 filed Mar. 4, 1997, also claims Provisional for No. 60/012,910 filed Mar. 6, 1996.

BACKGROUND OF THE INVENTION

The present invention relates to implantable stimulation devices, e.g., cochlear prothesis used to electrically stimulate the auditory nerve, and more particularly to an implantable receiver and corresponding external (not-implanted) transmitter, inductively coupled with the implantable receiver, and a set of special tools, or a tool kit, that facilitates a method of implanting the implantable receiver so that it may be properly aligned with the external transmitter without the use of magnets in either the implantable receiver or external transmitter.

Cochlear stimulation systems are known in the art. Such systems are used to help the profoundly deaf (those whose inner ear is dysfunctional, but whose auditory nerve remains at least partially intact) to hear. The sensation of hearing is achieved by directly exciting the auditory nerve with controlled impulses of electrical current, which impulses are generated as a function of perceived audio sounds. The audio sounds are picked up by a microphone carried externally (not implanted) by the deaf person and converted to electrical signals. The electrical signals, in turn, are processed and conditioned by an external speech processor in an appropriate manner, e.g., converted to a sequence of pulses of varying width and/or amplitude, and then transmitted to an implanted receiver circuit. The implanted receiver circuit is connected to an implanted electrode array that has been inserted into the cochlea of the inner ear. Electrical current is applied to individual electrode pairs of the electrode array by the implanted receiver circuit as a function of the processed signal it receives from the external speech processor (which in turn is based on the audio sounds picked up the external microphone). It is this electrical current which directly stimulates the auditory nerve and provides the user with the sensation of hearing.

A typical cochlear stimulation system as is known in the art includes an external (not implanted) speech processor connected to a headpiece via a cable. A microphone is typically mounted to, or made an integral part of, the headpiece. Audio sounds sensed by the microphone are converted to corresponding audio signals which are sent to the speech processor. These signals are processed by the speech processor in accordance with a selected speech processing strategy. The processed signals are then sent back to the headpiece to one or more coils which inductively couple these signals to corresponding coils in an implanted receiver. The implanted receiver may also be referred to as an implanted cochlear stimulator (ICS). The ICS is integrally connected to a cochlear electrode array which is inserted into the snail-shaped cochlea of the inner ear of the user using known surgical techniques and tools. The electrode array includes a plurality of individual electrodes which are paired in an appropriate manner for electrical stimulation of the cochlea.

In order for the signals to be efficiently coupled from the external headpiece to the ICS through the inductive link created by the external and implanted coils, it is necessary for the headpiece coil to be properly aligned with the implanted coil. Heretofore, such alignment has been achieved by placing a magnet in the headpiece that aligns the headpiece with a corresponding magnet in the ICS. Such magnet also holds the headpiece in place on the head of the user. See, e.g., U.S. Pat. No. Re. 32,947.

For some users, the headpiece is easily hidden under a nice crop of hair or attractive clothing or head gear. For other users, however, the headpiece cannot be easily hidden, leaving such users very conscious and ill-at-ease in wearing the headpiece. Improvements are needed, therefore, in the way that alignment is achieved between the headpiece and implanted receiver that allow all users to easily and comfortably wear the headpiece without being self-conscious of its presence.

Regardless of the type of implant involved (i.e., regardless of whether the implant is part of a cochlear stimulation system or some other device, e.g., a neural stimulator), the magnet used in prior art implanted receivers (to achieve and maintain proper alignment between the external and implanted coils) prevents, or is very detrimental to the effective use of, magnetic resonance imaging (MRI) techniques in the vicinity of the implanted magnet (which would typically include, for a cochlear stimulation system, the entire head region). Because MRI is an extremely valuable medical diagnostic tool (used by medical personnel to identify, locate, and treat a myriad of problems which could arise in any patient), deaf or other patients who are candidates for implantable stimulation systems would very much like the option of being able to use MRI, should the need arise for such use. Hence, there is a need in the art for other ways—ways which do not involve the use of an implanted magnet—to achieve the needed alignment between the external and implant coils.

SUMMARY OF THE INVENTION

The present invention addresses the above and other needs by providing a magnetless implantable receiver and corresponding magnetless external (not-implanted) transmitter, and a set of implant tools (or tool kit) that facilitates the implantation and alignment of the receiver with the external transmitter. Like prior art devices, the implantable receiver is adapted to be implanted in living tissue to perform a desired function, e.g., stimulate a nerve, and the external transmitter is adapted to be inductively coupled with the implantable receiver so that, when properly aligned, power and control information may be efficiently transmitted to the implantable receiver so that it can carry out its intended function. Unlike prior art devices, however, neither the transmitter nor implantable receiver used in accordance with the present invention utilize a magnet to maintain the needed alignment and coupling between the implanted receiver and the external transmitter. Rather, a special set of implant tools, or an implant tool kit, and method of using such tools, is provided to assure that the needed alignment and coupling are achieved and maintained between the implantable receiver and external transmitter when the implant operation is performed.

The external transmitter used with the present invention is worn or carried by the patient at a known location on or near the skin surface that is relatively easy to maintain. For example, for a cochlear stimulation system, the external transmitter (wearable processor) is worn behind the ear of the patient, much like a conventional hearing aid. For other types of stimulation systems, the external transmitter may be worn or carried in a belt, wrist band, ankle band, sock, or other article of clothing that can consistently be positioned over a desired skin location.

The set of tools, or tool kit, used with the invention include: (1) an external marker template; (2) a drilling template; (3) a subcutaneous marker template; and (4) a receiver dummy.

The external marker template is used to mark a desired implant location on the skin of the patient. This desired implant location will preferably be a location where sufficient bone or other hard tissue exists to allow a cavity or bed to be carved or formed wherein the implant receiver may be placed. Such a cavity/bed, once formed, thus helps secure or hold the receiver in a fixed implanted location. Conventional scanning and/or imaging techniques, e.g., computerized axial tomography (CAT), may first be implemented as required in order to identify a location where the bone thickness is sufficient for such a bed to be formed.

The drilling template is placed over and aligned with the implant location (marked using the external marker template) to mark and incise a location where a plurality of screws may be screwed into the patient's bone (or other hard tissue) in a prescribed pattern and orientation relative to the marked implant location on the skin of the patient. After the screws have been inserted, the incisions made in the skin for the screws are closed.

After the screw-hole incisions have been closed, a larger incision is then made in the patient, as needed, and the upper layers of skin and tissue are laid back to expose the screws that were previously inserted using the drilling template. The subcutaneous marker template includes a plurality of holes, or other keys, which align with the screws. The subcutaneous template is laid over and aligned with the screws, and is then used to mark the location of a subcutaneous bed wherein a cavity may be formed in which the receiver may be implanted.

After the location of the cavity (or bed) has been marked using the subcutaneous marker template, the cavity/bed is then formed in the tissue and/or bone using conventional surgical techniques. As the cavity/bed is being formed, the receiver dummy (which has the same shape and size as the actual receiver to be implanted, except that it has a protruding handle on one side to facilitate insertion and removal of the dummy from the implant cavity) may be removably inserted into the cavity/bed to test the cavity/bed for the proper size and depth.

Once a cavity/bed of the proper size has been formed, the actual implantable receiver is placed in the cavity/bed; the electrode array connected to the receiver is implanted or positioned as necessary in order to contact the desired tissue to be stimulated (e.g., the electrode array connected to the receiver is inserted into the cochlea); the receiver is sutured in place within the cavity/bed as needed; and the incision is closed by pulling the layer(s) of tissue and skin back over the implantable receiver and suturing the incision closed.

It is a feature of the invention to provide an implantable stimulator, adapted to be coupled to an external controller/transmitter, which avoids the use of magnets within the implantable stimulator.

It is another feature of the invention to provide a set of tools that facilitate the implantation and alignment of an implantable medical device, e.g., a tissue-stimulator device, with an external controller/transmitter that is inductively coupled with the implantable medical device.

BRIEF DESCRIPTION OF THE DRAWINGS

The above and other aspects, features and advantages of the present invention will be more apparent from the following more particular description thereof, presented in conjunction with the following drawings, wherein.

Corresponding reference characters indicate corresponding components throughout the several views of the drawings.

DETAILED DESCRIPTION OF THE INVENTION

The following description is of the best mode presently contemplated for carrying out the invention. This description is not to be taken in a limiting sense, but is made merely for the purpose of describing the general principles of the invention. The scope of the invention should be determined with reference to the claims.

Figure 1:
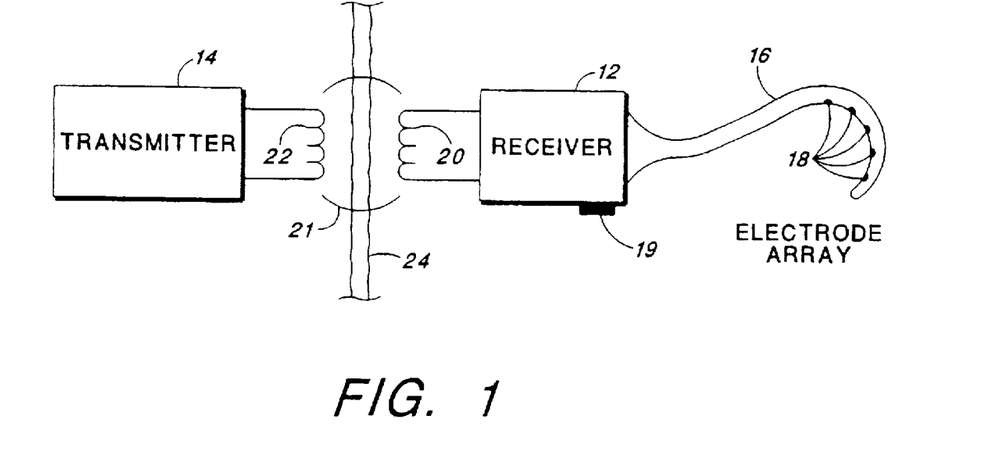
FIG. 1 is a block diagram of an external transmitter and implantable receiver which are inductively coupled to each other through aligned external and implanted coils.

Referring to FIG. 1, the present invention provides a magnetless implantable receiver 12, and a method of implanting such receiver, so that it may be properly aligned with an external transmitter 14. The implantable receiver 12 has an electrode array 16 attached thereto, which array includes a plurality of individual electrode contacts 18. It is the function of the implantable receiver 12 to selectively stimulate body tissue that is contacted by, or in the vicinity of, the electrode contacts 18. To this end, respective ones of the electrode contacts 18, and/or a common return electrode 19 (shown in FIG. 1 as part of the case of the receiver 12, but which could be located anywhere), are paired by electronic circuitry within the receiver 12 so that a stimulating electrical pulse may be applied between the selected electrode pair in order to stimulate the body tissue.

The implantable receiver 12 typically receives operating power and control commands from the external transmitter 14 via an inductive coupled link 21 formed between an implant coil 20 and an external coil 22. The link 21 thus spans through a layer of skin 24. In operation, the external coil 22 and the implant coil 20 may be considered as the primary and secondary windings, respectively, of a transformer, which transformer has an air gap separating the coils that includes the layer of skin 24. Thus, a carrier signal applied to the winding 22 is inductively coupled to the implanted coil 20. Such signal may be rectified and filtered to provide operating power for the receiver 12. Further, such signal may be modulated at the transmitter with control information. Such control information may be recovered in the receiver 12 using a suitable demodulator circuit.

Efficient signal transfer through the inductively coupled coils 20 and 22 is achieved when the two coils are properly aligned. That is, when coil 22 is properly aligned with coil 20, the magnetic field created by an alternating modulated signal applied to coil 22 passes through the majority of the windings of coil 20 so that a signal is induced at coil 20 which faithfully represents the signal applied to coil 22. Maintaining a proper alignment between coils 20 and 22 is thus a prerequisite for proper operation and control of the implanted receiver 12. Heretofore, as indicated previously, such alignment has been achieved by including a permanent magnet near the coil 20 of the receiver 12 which self-aligns with a permanent magnet near the coil 22 of the transmitter 14. In accordance with the present invention, however, no magnets are used within the implantable receiver 12 or the external transmitter 14.

Implantable simulators, such as the receiver 12 and electrode array 16 and implant coil 20 shown in FIG. 1, are known in the art, as are external transmitters used to control such simulators. See, e.g., U.S. Pat. Nos. 4,267,410; 4,819, 647; 4,019,518; 4,207,441; 4,428,377; 4,991,582 and 4,532, 930; all of which patents are incorporated herein by reference. A particular type of implantable tissue stimulator having applicability to the present invention is an implantable cochlear stimulator (ICS) of the type disclosed, e.g., in U.S. Pat. No. 5,531,774, also incorporated herein by reference. It is to be emphasized, however, that the present invention is not intended to be limited to an implantable cochlear stimulator of the particular type disclosed in the referenced patent. Rather, the invention may be used with any type of implantable receiver 12 that needs to be aligned with an external transmitter 14.

The invention, rather than being directed to particular types of circuitry used within the implantable receiver 12 or external transmitter 14, is directed to a particular technique for implanting the receiver 12 so that its implanted coil 20 may be aligned (without the use of magnets) with the coil 22 of the external transmitter 14. As such, the invention has nothing to do with the particular circuitry used inside of the implantable receiver 12 or the external transmitter 14. That is, the invention may be used with any type of implantable receiver 12 and external transmitter 14, regardless of the circuitry used therein, where a coil or antenna of the implantable device must be properly aligned with a corresponding coil or antenna of an external device.

Figure 2A:
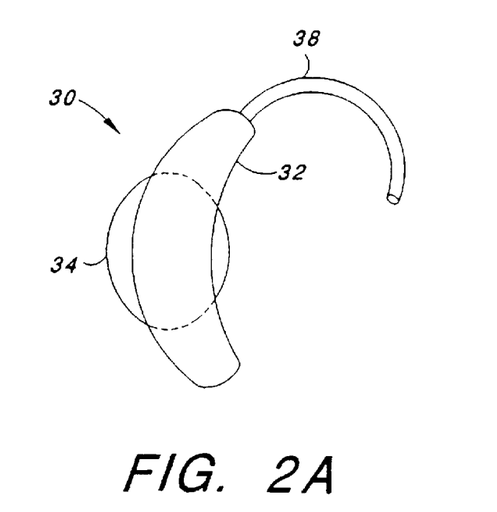
FIG. 2A shows a side view of a behind-the-ear (BTE) speech processor that may be used as the external transmitter of the system shown in FIG. 1.
Figure 2B:
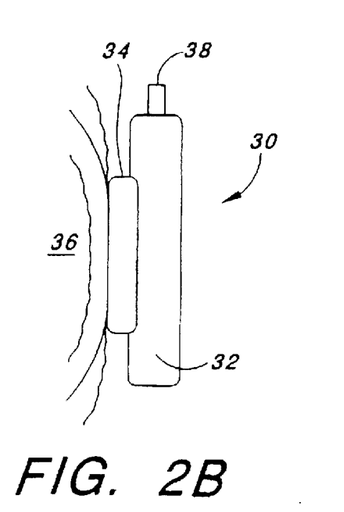
FIG. 2B shows an end view of the BTE speech processor of FIG. 2A.
Figure 3:
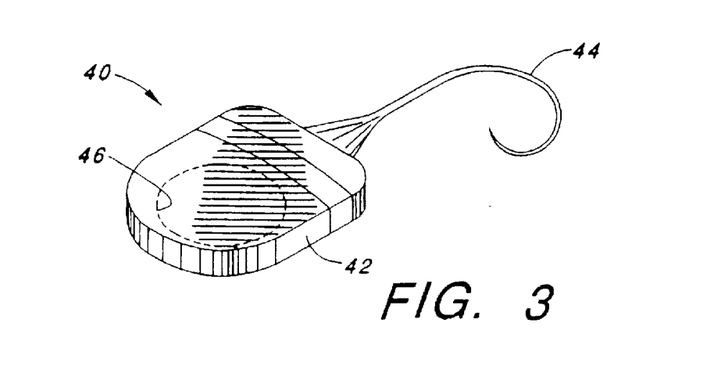
FIG. 3 is a perspective view of an implantable cochlear stimulator (ICS), including the electrode array that forms an integral part thereof.

While the invention may be used with any type of implantable receiver 12 that needs to be aligned with an external transmitter 14, as shown in FIG. 1, the best mode currently contemplated for practicing the invention is with an implantable cochlear stimulator (ICS) and a corresponding external speech processor, or wearable processor (WP) 30. FIGS. 2A and 2B respectively show side and end views of a behind-the-ear (BTE) speech processor 30, or external transmitter, that may be used with the invention. FIG. 3 illustrates a perspective view of an ICS 40, including an ICS housing 42 and electrode array 44, that may be used with the invention. The ICS housing 42 includes a coil therein, which coil is generally a rounded pancake type coil which is located near the rounded end of the housing 42, as shown by the dotted line 46. Unlike prior art ICS devices, the ICS 40 of FIG. 3 does not include a magnet. As a result, the ICS 40 is somewhat lighter (weighs less) than prior art ICS devices.

The BTE processor 30 (FIGS. 2A & 2B) includes a main section 32, wherein most of the speech processing circuitry is housed, and a headpiece section 34, where an external coil, such as the coil 22 of FIG. 1, is housed. The coil within the headpiece section 34 is generally a flat pancake type coil as is known in the art. The main section 32 includes an ear hook 38 adapted to fit over the ear of a patient, or user, so that the entire processor 30 may be comfortably worn behind the ear of the user, much like a conventional hearing aid. When fitted behind the ear of the user, the headpiece section 34 rests comfortably against the head 36 (FIG. 2B) of the user.

Figure 4:
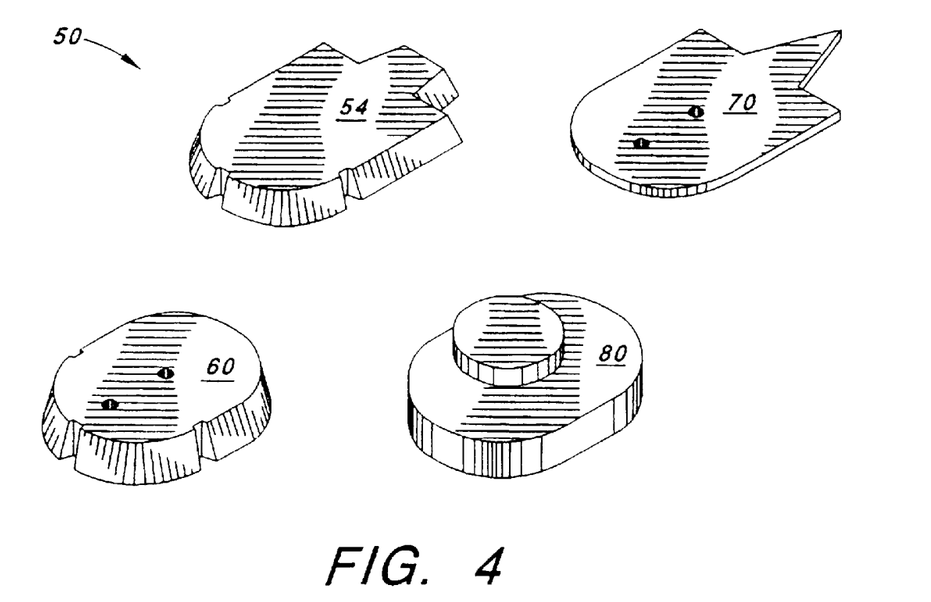
FIG. 4 shows an implant tool kit that may be used with the invention, which tool kit includes: (1) an external marker template, (2) a drilling template, (3) a subcutaneous marker template, and (4) a receiver dummy.

The exact location at which the headpiece 34 contacts the tissue of the head 36 is adjustable, within certain tolerances, by bending and forming the hook 38. However, in order to achieve optimum inductive coupling between the coil within the headpiece 34 and the coil within the corresponding ICS 40, it is generally necessary for the ICS 40 to be implanted in a fairly precise location relative to where the headpiece 34 will be positioned when the processor 30 is worn behind the user's ear. To that end, the present invention provides a set 50 of implant tools, or toolkit 50, as shown in FIG. 4. Such toolkit 50 includes four main elements or tools: an external marker template 54, a drilling template 60, a subcutaneous marker template 70, and a receiver dummy 80. Other incidental elements commonly used during a surgical procedure, such as a screwdriver, a knife blade and holder, surgeon marking pens, suturing needles and thread, etc., as described below, may likewise be included in the toolkit 50, if desired.

Figure 5A:
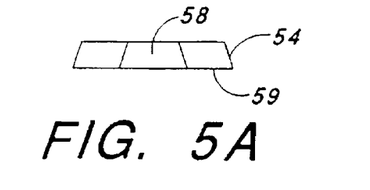
FIGS. 5A, 5B and 5C are end, top, and side views, respectively, of the external marker template included in FIG. 4.
Figure 5B:
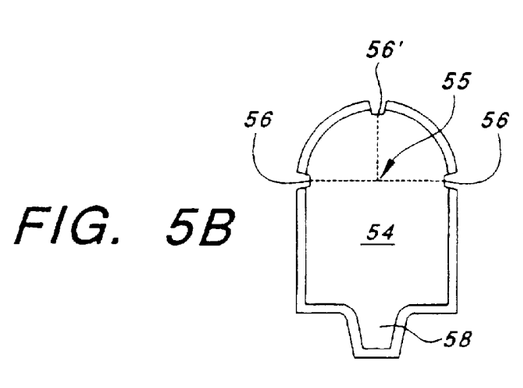
Figure 5C:
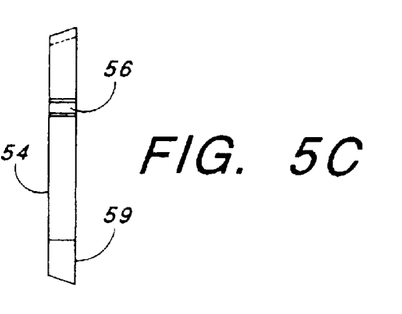

The external marking template 54 is shown in greater detail in FIGS. SA, 5B and 5C, which show end, top and side views of the template 54, respectively. As seen in these figures, the template 54 has an overall shape and size that is the same as the overall shape and size as the main body portion 42 of the ICS 40. Indentations 56 and 56' mark the general location or coordinates of the coil within the body 42. That is, the mid point 55 of a line drawn between the two side indentations 56 (which mid point 55 also coincides with an extension of the end indentation 56') defines the approximate center of the location within the ICS body 42 where the coil is located. A neck portion 58 of the template 54 identifies the end of the ICS where the electrode array is connected. Preferably, the template 54 has slopping edges to facilitate the use of a marker pen to trace the outline defined by the template on the skin of a patient within whom the ICS is to be implanted. That is, in use, the marker template 58 is laid on the patient at the location where the ICS is to be implanted so that a bottom side 59 of the template is against the patient's skin. A suitable marking pen, such as a surgeons marking pen, is then used to trace the outline defined by the template on the patient's skin. The marker template 54 may be made from any suitable material, such as plastic.

Figures 6A, 6B, 6C:
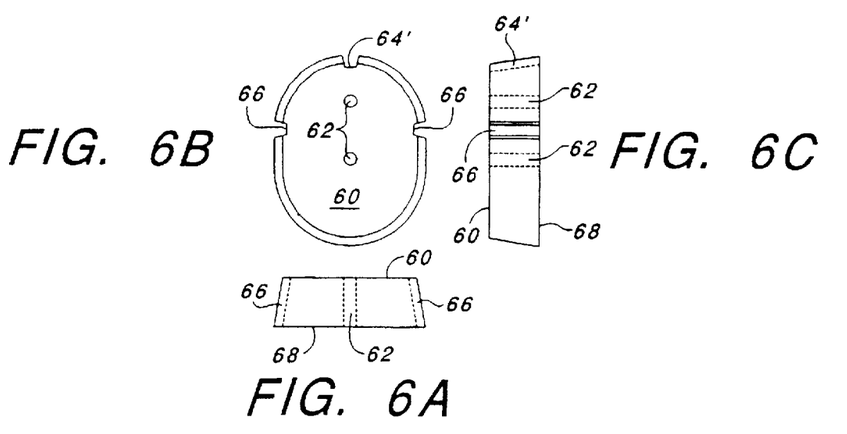
FIGS. 6A, 6B and 6C are end, top, and side views, respectively, of the drilling template included in FIG. 4.

FIGS. 6A, 6B and 6C show an end, top, and side view, respectively, of the drilling template 60. The drilling template 60 has a size that is generally the same as the rounded end of the marking template 54. Thus, once the outline of the ICS has been marked on the skin of the patient using the marker template 54, the drilling template 60 can be laid over the marked outline. Indentations 64' and 66 along the edges of the drilling template 60 are generally positioned to correspond with the indentations 56' and 56 of the marker template 54. Two spaced-apart alignment holes 62 are located generally along a central longitudinal axis of the template 60. These holes 62 pass all the way through the template 60. The template 60 may be made from any suitable material, e.g., stainless steel or hard plastic. The template 60 typically will be quite thick, having a thickness of at least ⅓ its width, where its width is roughly the distance between the indentations 66, seen in FIG. 6B, and its thickness is the length of the holes 62 shown in FIGS. 6A and 6C.

Figures 7A, 7B:
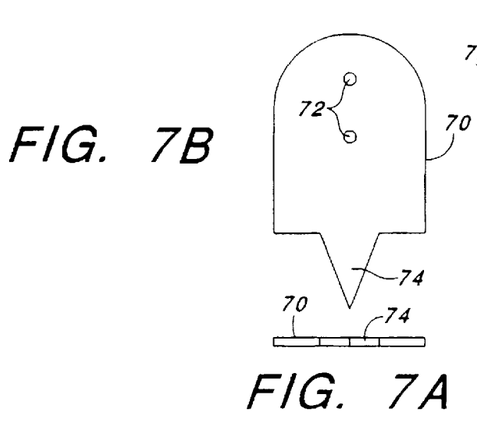
FIGS. 7A, 7B and 7C are end, top, and side views, respectively, of the subcutaneous marker template included in FIG. 4.
Figure 7C:
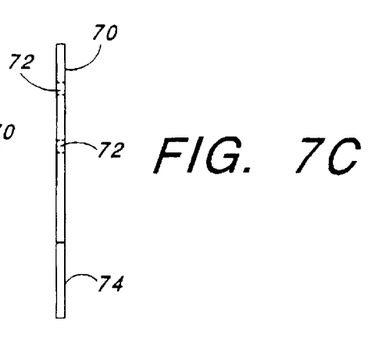

FIGS. 7A, 7B and 7C show an end, top, and side view, respectively, of the subcutaneous marker template 70. The subcutaneous marker template 70 has a size that is generally the same as the width and length of the ICS 40 to be implanted, which is the same size as the marking template 54. Once an incision has been made and one or more layers of skin have been removed to expose the screws that are inserted into the patient's bone/tissue using the drilling template 60 (as explained more fully below), the subcutaneous marker template 70 is aligned with such screws, and then used to mark the location where a pocket or cavity for the ICS 40 is to be made. Two spaced-apart alignment holes 72 are located generally along a central longitudinal axis of the template 70, and are spaced apart the same distance as the holes 62 in the drilling template 60. Thus, the screws inserted and drilled into the bone/tissue using the drilling template 60 (described below) fit within the holes 72 when the template 70 is laid over such screws. Once the template 70 is in place, a surgical marker (not shown) is used to trace around the edges of the template in order to mark the subcutaneous location where the implanted ICS 40 is to be positioned. After the subcutaneously location has been marked using the template 70, the screws can be removed. Typically, the subcutaneous template 70 is made from stainless steel, or a hard plastic, and (like any implant element or surgical tool) must be made sterile prior to use. At one end of the template 70, a taper point 74 is located to represent that end of the ICS 40 from which the wires going to the cochlear electrode array 44 (FIG. 3) are located.

Figure 8A:
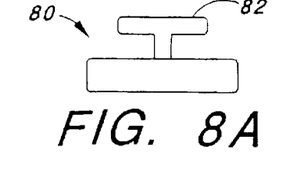
FIGS. 8A, 8B and 8C are end, top, and side views, respectively, of the external marker template included in FIG. 4.
Figure 8B:
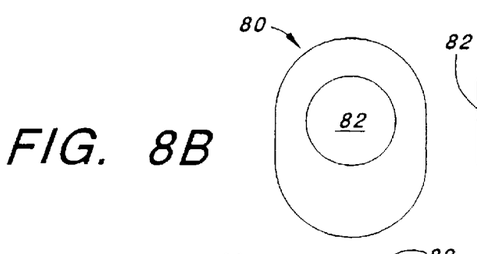
Figure 8C:
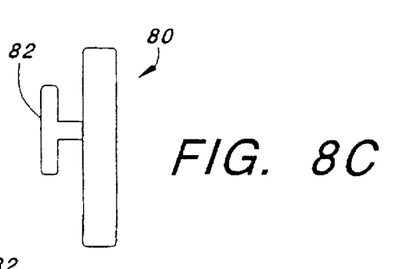

FIGS. 8A, 8B and 8C show an end, top, and side view, respectively, of the ICS dummy 80. The ICS dummy, as its name implies, is made to have the same physical size and shape (minus the electronic circuitry) as the housing or body 42 of the ICS to be implanted. A knob 82 facilitates holding the dummy 80 as it is inserted into and removed from a body cavity, as such cavity is formed in the bone/tissue of the patient at the location marked using the subcutaneous marker template 70. Typically, the receiver dummy 80 is made using a suitable mold filled with a hard or semi-hard plastic, or other formable material, such as silicone rubber or epoxy.

Figure 9:
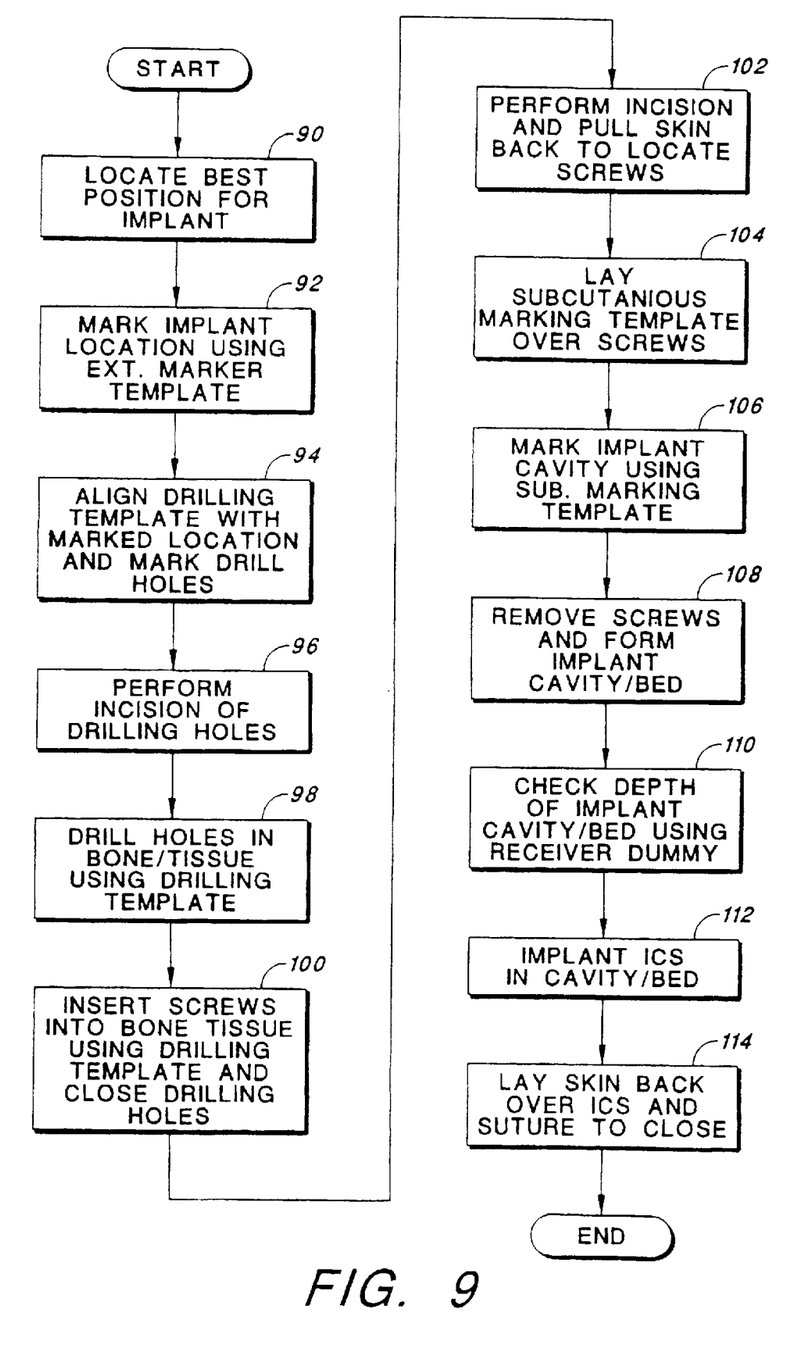
FIG. 9 is a flow chart that illustrates a method of implanting an implantable receiver using the tool kit of FIG. 4.

Referring next to FIG. 9, a flow chart is shown that illustrates the method or technique used in accordance with the present invention to implant an ICS 40 so that it will be implanted at a desired location. Each main step in the flow chart of FIG. 9 is represented as a separate "block" or "box", with each block or box having a reference numeral assigned thereto for ease of explanation.

As seen in FIG. 9, a first step of the implant method or technique, shown at block 90, is to identify the best position for the device to be implanted. Any suitable technique may be used to complete this step including general knowledge regarding the anatomy of the patient, performing a CAT scan (preferred), feeling and probing, and the like. Typically, a location is selected where the thickness of the bone/tissue is sufficient to support making a cavity for the implant device. Also, for a BTE cochlear transmitter 30 of the type shown in FIGS. 2A and 2B, an implant location for the ICS 40 is selected that is generally behind the ear and more or less alignable with an external processor 32 that is worn behind the patient's ear.

Figure 10A:
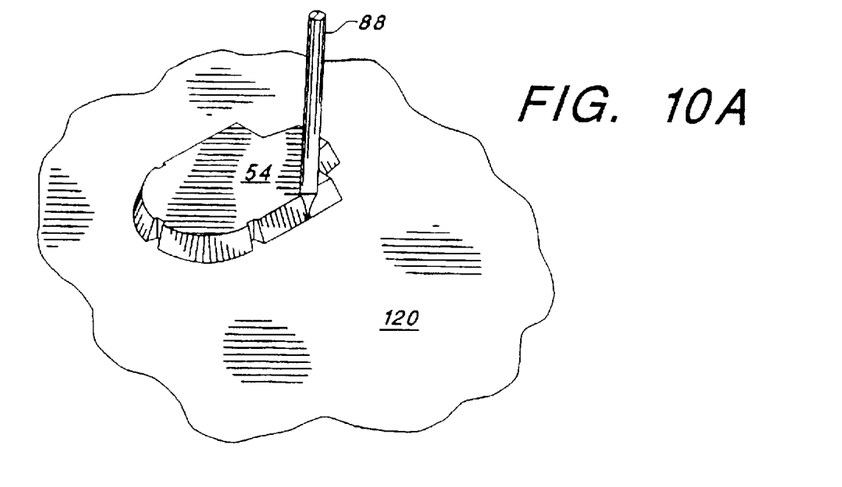
FIGS. 10A–10H illustrate various steps associated with the implant technique or method depicted in FIG. 9.
Figures 10B, 10C:
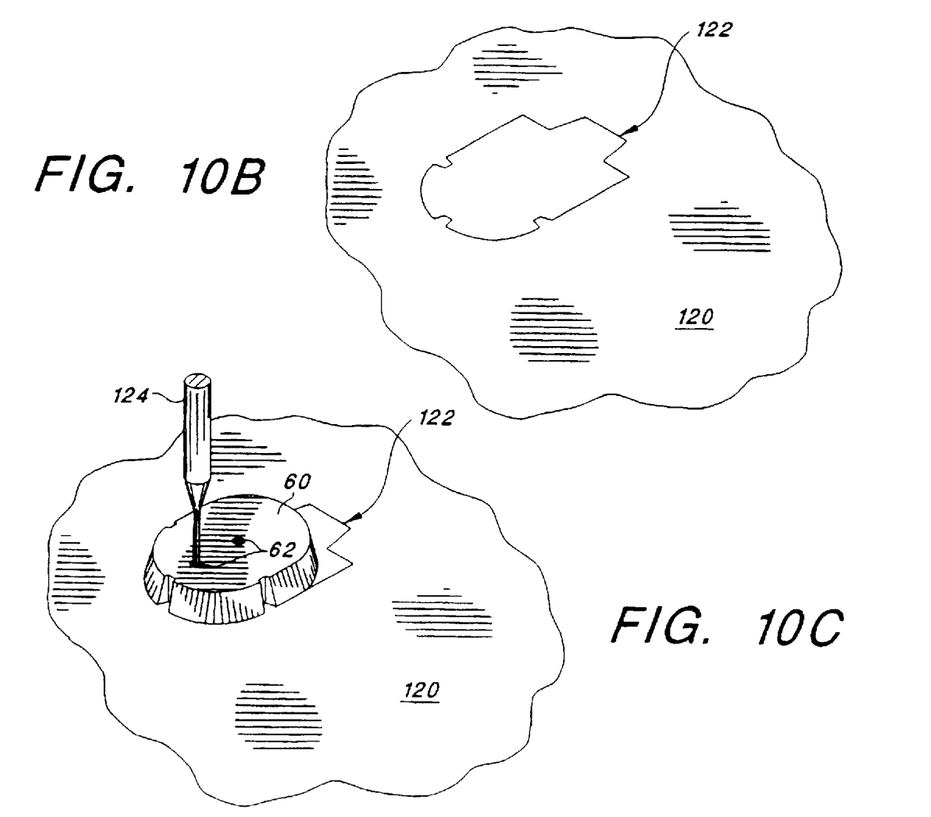

Once the desired implant location has been identified (block 90), the external marker template 54 is laid on the patient's skin 120 at the desired implant location, and the implant location is marked using a suitable surgeon's marking pen 88 (block 92) that traces around the edges of the template 54, as depicted in FIG. 10A. When the external marker template 54 is removed, then the implant location 122 is clearly visible on the skin 120 of the patient as shown in FIG. 10B.

After the implant location has been marked, the drilling template 60 is laid over and visually aligned with the marked location 122. Drill holes are then marked on the skin by inserting a suitable thin marking tool through the holes 62 of the drilling template (block 94, FIG. 9). The drilling template is then removed, and the drill holes are incised (block 96) using any suitable surgical incision technique. The drilling template 60 is then placed back over the marked implant location 122. A suitable (conventional) small diameter surgical drill is then guided, using the drill holes 62 in the drilling template 60, to drill a pair of holes in the bone/tissue to a desired depth (block 98). Alternatively, with the location of the two holes marked on the skin, a surgeon, using the point of a surgeon's knife, can generally fashion two holes through the skin and tissue of the patient to a desired depth.

Once the holes have been drilled or otherwise formed, an implantable screw 126 is screwed into each of the holes so as to lodge subcutaneously in the bone/tissue of the patient (block 100, FIG. 9). This process is facilitated using the drilling template 60 and a suitable screw driver 124, as illustrated in FIG. 10C. Once the screws have been inserted into the bone/tissue of the patient, the screw holes in the skin are surgically closed, e.g., using suturing thread, as required.

Figure 10D:
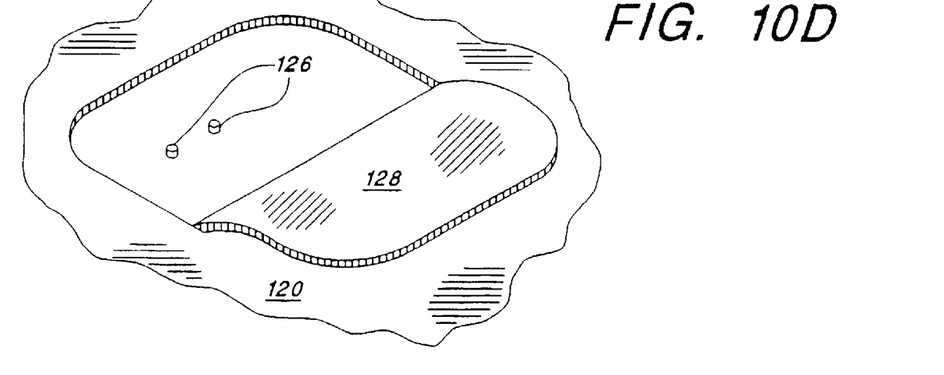
Figure 10E:
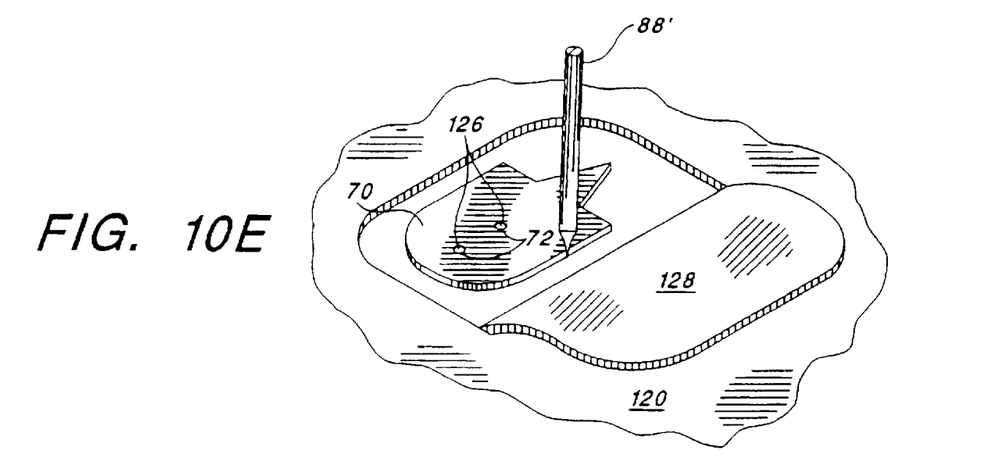
Figure 10F:
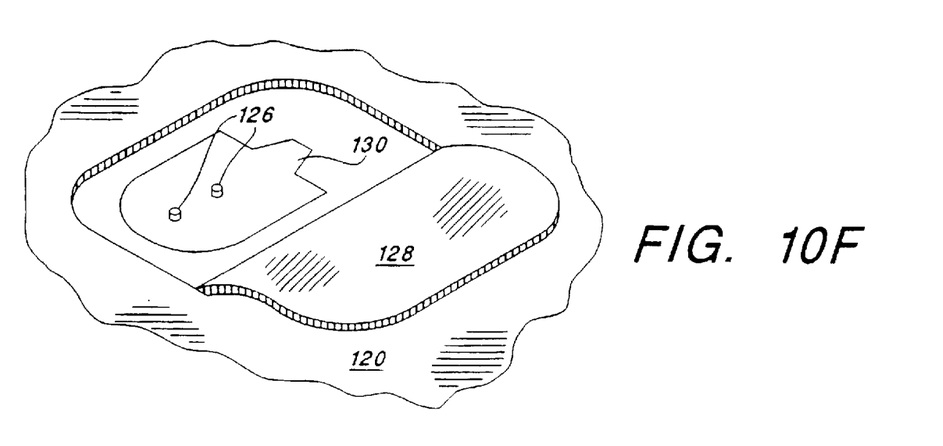

Once the screw holes are closed, an incision is next made near the marked implant location 122 so that a layer 128 of skin/tissue may be laid back in order to expose the two screws 126 previously inserted (block 102, FIG. 9), as seen in FIG. 10D. With the two screws 126 exposed, the subcutaneous marker template 70 is laid over the screws so that each screw 126 is aligned with and inside of the corresponding hole 72 of the template 70, as illustrated in FIG. 10E. A surgical marking pen 88' may then be used to trace around the edge of the template 70 in order to subcutaneously mark the location where the cavity or bed for the implant device is to be formed (block 106, FIG. 9). Alternatively, a surgeon's knife may be used to trace around the edges of the temple, placing an incised mark around the template. The template 70 may then be removed, leaving the location of the implant cavity marked as a line 130 or other identifying indicia, as illustrated in FIG. 10F.

Figure 10G:
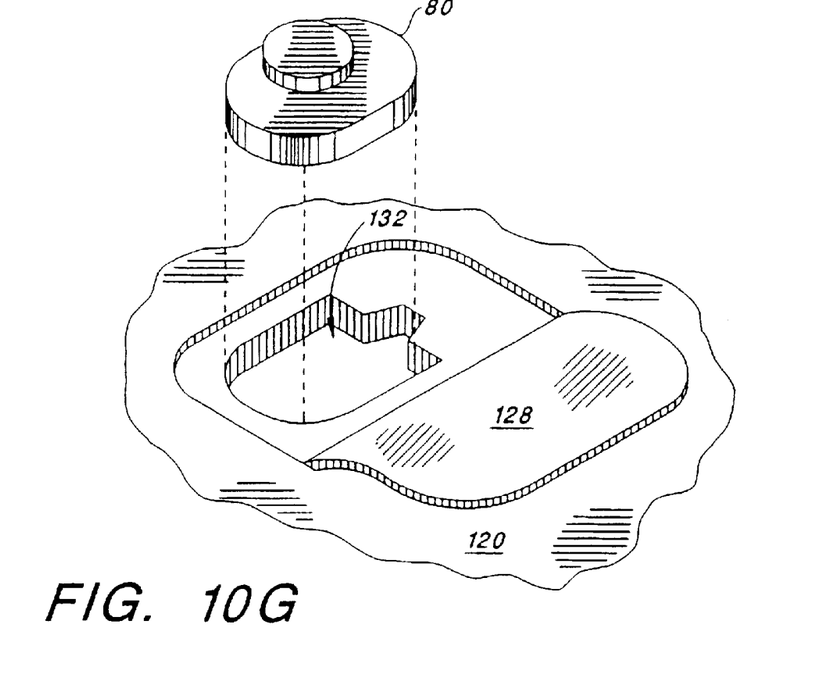

The two screws 126 are removed and a cavity or bed 132 is formed for the implant device in the bone/tissue at the location previously marked (block 108, FIG. 9). As the cavity or bed 132 is formed, it is regularly checked using the receiver dummy 80 for proper size and depth (block 110), as illustrated in FIG. 10G. Once the proper size and depth have been achieved, the ICS 40 is implanted in the cavity/bed thus formed (block 112, FIG. 9), and the electrode array 44 (FIG. 3) is inserted/implanted so as to make contact with the desired tissue location.

Figure 10H:
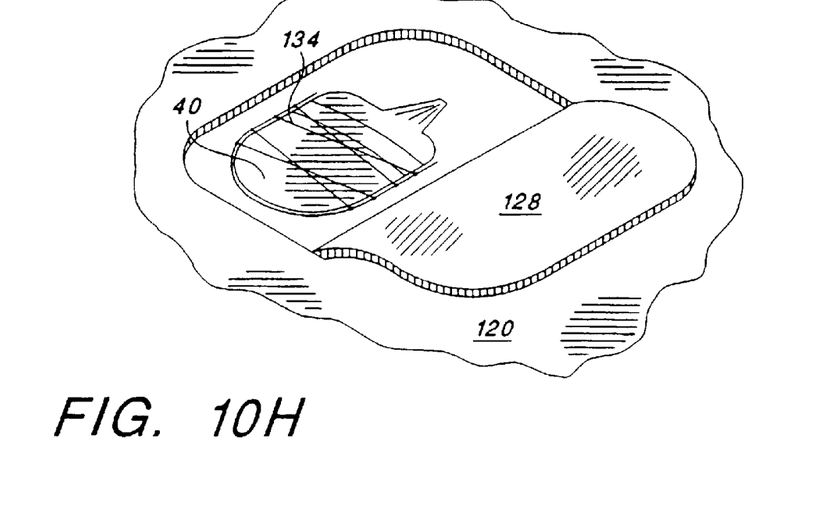

Once implanted and tested, the ICS 40 is sutured into the cavity/bed 132 using any suitable surgical suturing thread or material 134, as seen in FIG. 10H. The layer 128 of tissue/skin is then laid back over the ICS, and the incision is sutured closed (block 114, FIG. 9), thereby completing the implant procedure.

Once the ICS 40 has been implanted as above described, it is advantageously implanted so as to be aligned with the desired implant location 122 (FIG. 10B) originally marked before the implant operation was performed. Hence, by positioning the external coil or headpiece 34 (FIG. 2A, 2B) to be over this known location, a proper alignment is achieved and maintained between the implanted ICS 40 (FIG. 4) and the external coil/headpiece, without the use of magnets in the implanted receiver device or the external transmitter device. Thus, it is seen that the invention allows the receiver and transmitter to both be magnetless; and provides alignment means for achieving and maintaining a proper alignment between the implantable receiver and external transmitter. It is further seen that such alignment means include, inter alia, a set of alignment tools used to implant the receiver in a known location relative to an external reference point; and means (e.g., an external transmitter worn behind the ear at a known location relative to the ear) for positioning the external transmitter at the known location relative to the external reference point.

As described above, it is seen that the present invention provides an implantable stimulator, adapted to be coupled to an external controller/transmitter, which avoids the use of magnets within the implantable stimulator. More particularly, it is seen that the invention provides a way to achieve an exact location of the implant device relative to the external transmitter. Such exact location would not be achievable without using the supercutaneous marking, inserting alignment screws, cutting, subcutaneous marking-relative-to-the-alignment-screws, implanting, and closing procedure taught by the present invention. This is because, e.g., without using the subcutaneous marking screws and associated templates as taught by the present invention, the moment one dissects the skin and the underlying soft tissue, the tissue situation is altered, and one could never be certain that a desired alignment was actually being achieved.

While the invention herein disclosed has been described by means of specific embodiments and applications thereof, numerous modifications and variations could be made thereto by those skilled in the art without departing from the scope of the invention set forth in the claims.

What is claimed is:

1. A magnetless implantable stimulator system comprising an implantable receiver (12) and an external transmitter (14), each having respective coils (20, 22) which, when aligned to provide inductive coupling therebetween, allow power and data signals to be coupled between the transmitter and receiver, wherein the implantable receiver (12) and external transmitter (14) are both magnetless; and further comprising alignment means for achieving and maintaining a proper alignment between the implantable receiver and external transmitter, said alignment means comprising a set of alignment tools (50) used to implant the receiver in a known location relative to an external reference point; and means for positioning (38) the external transmitter at the known location relative to the external reference point.

2. The implantable receiver (14) and external transmitter (12, 30) as set forth in claim 1 wherein the receiver comprises an implantable cochlear stimulator (ICS) (40), and wherein said external reference point comprises an ear of a patient's head, and wherein said positioning means comprises means for wearing the external transmitter (30) behind the ear.

3. The implantable receiver and external transmitter as set forth in claim 1 wherein said set of alignment tools comprises:

an external marker template (54) usable to mark a desired implant location on the skin of the patient, a drilling template (60) usable to screw a plurality of screws into the patient's tissue/bone at a prescribed location relative to the marked implant location on the skin of the patient, a subcutaneous marker template (70) usable to mark a location of a subcutaneous bed wherein a cavity may be formed in which the receiver can be implanted, said subcutaneous marker being keyed to the plurality of screws screwed into the patient's bone after incising the patient's head, and a receiver dummy (80) that may be removably inserted into the cavity as it is formed to test the cavity for the proper size and depth, said receiver dummy having a shape and size substantially the same as the implantable receiver.

4. The implantable receiver and external transmitter as set forth in claim 3 wherein the drilling template (60) has a plurality of holes (62) therethrough arranged in a prescribed spaced-apart pattern relative to each other, and wherein said subcutaneously marker template (70) also has a plurality of holes (72) therethrough arranged in a pattern that matches the spaced-apart pattern of the holes of the drilling template, whereby the subcutaneous marker template may be positioned over and aligned with holes made using the drilling template.

5. The implantable receiver and external transmitter as set forth in claim 4 further including a plurality of implantable screws (126), respective ones of which may be screwed into tissue/bone of the patient at the locations defined by the plurality of holes of the drilling template.

6. The implantable receiver and external transmitter as set forth in claim 5 wherein said implantable screws (126) are small screws that are implanted subcutaneously through holes in the skin made using the drilling template (60).

7. The implantable receiver and external transmitter as set forth in claim 6 wherein the subcutaneous marker template (70) includes means for aligning (72) it with with the implanted subcutaneous screws when a layer of the patient's tissue/skin is pulled back to expose the implanted subcutaneous screws.

8. A method of implanting an implantable receiver device (12) at a known location relative to an externally-marked location, comprising the steps of:

(a) marking on the skin of a patient the location where the implantable receiver is to be implanted;

(b) aligning a drilling template with the location marked in step (a), said drilling template having a plurality of holes therethrough that mark a prescribed spaced-apart relationship between said plurality of holes;

(c) drilling a plurality of holes through the patient's skin to a desired subcutaneous depth using the drilling template of step (b) as a guide so that the plurality of holes maintain the prescribed spaced-apart relationship defined by the plurality of holes of the drilling template;

(d) implanting a plurality of screws into the patient's bone/tissue by inserting respective screws into each of the plurality of holes formed in step (c), the screws thus implanted maintaining the prescribed spaced-apart relationship defined by the plurality of holes of the drilling template;

(e) incising an area around the plurality of holes and folding back a layer of tissue/skin so as to expose the plurality of implanted screws;

(f) laying a subcutaneous marker template over the exposed implanted screws, said subcutaneous marker template having a plurality of holes therein arranged in a pattern that matches the prescribed spaced-apart relationship defined by the plurality of holes of the drilling template;

(g) marking a desired subcutaneous implant location for the implantable receiver using the subcutaneous marker template aligned with the plurality of screws in step (f);

(h) forming a cavity/bed for the implantable receiver at the location marked in step (g); and (i) implanting the implantable receiver within the cavity/bed formed in step (h), whereby the implant location is aligned with the implant location initially marked in step (a).

9. The method as set forth in step 8 wherein step (h) includes using a receiver dummy to help measure the size of the cavity/bed as it is being formed, said receiver dummy having a physical size and shape that is substantially the same size and shape as the implantable receiver.

* * * * *

UNITED STATES PATENT AND TRADEMARK OFFICE
CERTIFICATE OF CORRECTION

PATENT NO. : 6,141,591
DATED : October 31, 2000
INVENTOR(S) : Lenarz, Neurburger, Weber Page 1 of 1

It is certified that error appears in the above-identified patent and that said Letters Patent is hereby corrected as shown below:

Title page,
Change the order of inventors from:
   "Thomas Lenarz; Benno P. Weber; Jurgen Neuburger",
to:

-- Benno P. Weber; Jurgen Neuburger; Thomas Lenarz --

Signed and Sealed this

Twenty-fifth Day of December, 2001

Attest:

Attesting Officer

JAMES E. ROGAN
Director of the United States Patent and Trademark Office